United States Patent [19]
Goldberg

[11] Patent Number: 5,698,192
[45] Date of Patent: Dec. 16, 1997

[54] OCULAR IMPLANTS AND METHODS FOR THEIR MANUFACTURE

[75] Inventor: Eugene P. Goldberg, Duluth, Ga.

[73] Assignee: University of Florida, Gainesville, Fla.

[21] Appl. No.: 719,764

[22] Filed: Sep. 25, 1996

[51] Int. Cl.$^6$ ............................ A61K 31/79; C08F 2/46; C08G 63/91; B05D 3/00
[52] U.S. Cl. ..................... 424/78.18; 424/78.24; 522/84; 522/85; 522/149; 522/153; 427/294; 427/296; 427/299; 427/430.1; 427/495; 427/496; 427/498; 427/506
[58] Field of Search ................. 424/78.18, 78.24; 522/84, 85, 149, 153, 912, 915; 525/64, 937; 264/1.4, 22; 427/495, 496, 506, 498, 532, 595, 294, 296, 299, 430.1

[56] References Cited

U.S. PATENT DOCUMENTS

| | | | |
|---|---|---|---|
| 4,589,964 | 5/1986 | Mayhan et al. | 522/85 |
| 4,806,382 | 2/1989 | Goldberg et al. | 427/2 |
| 4,961,954 | 10/1990 | Goldberg et al. | 427/2 |
| 5,108,776 | 4/1992 | Goldberg et al. | 427/2 |
| 5,130,160 | 7/1992 | Goldberg et al. | 427/2 |
| 5,290,548 | 3/1994 | Goldberg et al. | 424/78.18 |

*Primary Examiner*—Thurman K. Page
*Assistant Examiner*—Kathryne E. Shelborne
*Attorney, Agent, or Firm*—Kerkam, Stowell, Kondracki & Clarke; Dennis P. Clarke

[57] ABSTRACT

A method for modifying an ocular implant polymer surface by the gamma-irradiation induced polymerization thereon of N-vinylpyrrolidone, 2-hydroxyethylmethacrylate or a mixture thereof while maintaining the following conditions:

(a) monomer concentration in the range of from about 0.1% to about 50%, by weight;

(b) total gamma dose in the range of from about 0.001 to less than about 0.50 Mrad; and (c) gamma dose rate in the range of from above about 2,500 to about $10^8$ rads/minute.

22 Claims, 1 Drawing Sheet

5,698,192

OCULAR IMPLANTS AND METHODS FOR THEIR MANUFACTURE

RELATED APPLICATION

The invention described in this application is related to those described in U.S. Pat. Nos. 5,108,776, 5,130,160 and 5,290,548 which are continuations-in-part of application Ser. No. 07/304,479 filed Feb. 1, 1989 (now U.S. Pat. No. 4,961,954) which is a continuation-in-part of application Ser. No. 07/037,153 filed Apr. 10, 1987 (now U.S. Pat. No. 4,806,382). The entire disclosures of each of the above-listed patents are incorporated herein by reference.

BACKGROUND OF THE INVENTION

1. Field of the Invention

The present invention relates to ocular implants and methods for improving surfaces thereof.

2. Discussion of the Prior Art

Studies have shown that the surgical implantation of ocular implants such as intraocular lenses (IOL) and the like can result in the loss of significant corneal endothelial tissue unless great care is taken to ensure a lack of contact between the device and the endothelium. Most ocular implants are constructed of hydrophobic polymethylmethacrylate (PMMA) polymers because of their superior optical qualities, resistance to biodegradation and the like. It has been found, however, that PMMA surfaces adhere to endothelial cells upon even casual contact and that separation of the surface therefrom results in a tearing away of the endothelial tissue adhered to the polymer surface. Similar adhesive interactions with other ocular tissues, i.e., the iris, can also cause adverse tissue damage. Other hydrophobic polymers which are used or have been proposed for use in ocular implants (i.e., polypropylene, polyvinylidene fluoride, polycarbonate, polysiloxane) also can adhere to ocular tissue and thereby promote tissue damage.

It is well documented in the prior art that a significant disadvantage inherent in PMMA IOLs resides in the fact that any brief, non-traumatic contact between corneal endothelium and PMMA surfaces results in extensive damage to the endothelium. See Bourne et al, Am. J. Ophthalmol., Vol. 81, pp. 482–485 (1976); Forster et al, Trans. Am. Acad. Ophthalmol. Otolaryngol., Vol. 83, OP-195-OP-203 (1977); Katz et al, Trans. Am. Acad. Ophthalmol. Otolaryngol., Vol. 83, OP-204-OP-212 (1977); Kaufman et al, Science, Vol. 198, pp. 525–527 (1977) and Sugar et al, Arch. Ophthalmol., Vol. 96, pp. 449–450 (1978) for a discussion of the problem associated with implant surface/endothelium contact.

Since it is extremely difficult to avoid any contact between implant surfaces and endothelium during surgical procedures, efforts have been undertaken to modify the PMMA ocular implant surfaces to reduce the tendency thereof to adhere to and damage corneal endothelium.

Ocular implant surfaces have been coated with various hydrophilic polymer solutions or temporary soluble coatings such as methylcellulose, polyvinylpyrrolidone [Katz et al, supra, and Knight et al, Chem. Abs., Vol. 92:203547f (1980)] to reduce the degree of adhesion between the implant surfaces and endothelial tissue cells. While offering some temporary protection, these methods have not proven entirely satisfactory since such coatings complicate surgery, do not adhere adequately to the implant surfaces, become dislodged or deteriorate after implantation, dissolve away rapidly during or soon after surgery or may produce adverse post-operative complications. Moreover, it is difficult to control the thickness and uniformity of such coatings.

Yalon et al [Acta: XXIV, International Congress of Ophthalmology, ed. Paul Henkind (1983)] attempted to produce protective coatings on PMMA implant surfaces by gamma-radiation induced polymerization of vinylpyrrolidone thereon. [See also Knight et al, supra.] Their efforts were not altogether successful, however, since their methods also presented problems in controlling the optical and tissue protective qualities of the coatings. Process conditions and parameters (i.e., monomer concentration solvent, dose and dose rate) were not specified. The resulting coatings were of poor quality and non-uniform mechanical stability.

Gamma-PVP treatment of PTFE has been reported, but under severe process conditions requiring gamma doses above 1 Mrad which are impractical in that both bulk and surface properties of the PTFE are changed [Boffa et al, J. Biomed. Mater. Res., Vol. 11, p. 317 (1977)]. Non-aqueous solutions of high monomer concentrations (50% NVP in pyridine) are required at relatively high doses of gamma radiation (1–5 Mrad), resulting in a high degree of grafting, but with extensive changes in the bulk and surface properties of the PTFE since PTFE is readily degraded at gamma doses above 1 Mrad.

In U.S. Pat. No. 4,806,382 issued Feb. 21, 1989, there are described improved methods for producing hydrophilic, gamma-irradiation induced polymerized and chemically grafted coatings on ocular implants constructed of a variety of polymeric materials, which methods overcome the above-noted difficulties and disadvantages.

The invention described in that application is predicated on the discovery of certain process conditions and parameters that produce thin hydrophilic gamma-irradiation induced polymerized and chemically grafted coatings of N-vinyl-pyrrolidone (NVP) [PVP], copolymerized NVP and 2-hydroxyethylmethacrylate (HEMA) [P(NVP-HEMA)], or HEMA [PHEMA] on the surfaces of ocular implants constructed of materials including polymethylmethacrylate (PMMA) and of other process conditions and parameters which produce thin gamma-irradiation induced graft PVP, P(NVP-HEMA), or PHEMA coatings on the surfaces of ocular articles constructed of materials including polypropylene (PP), polyvinylidene fluoride (PVDF), polycarbonate (PC) and silicone (PSi). The coatings increase the hydrophilicity of the implant surface and minimize adhesion between the surface and sensitive ocular tissues such as corneal endothelium or iris thereby minimizing tissue damage and post-operative complications occasioned by contact between the implant surface and ocular tissue. The coatings produced by the improved method of the invention described in U.S. Pat. No. 4,806,382 are thin and reproducibly uniform. Moreover, they are chemically bound to the surface of the ocular implant and, therefore, far more durable and less subject to removal, degradation or deterioration during or following surgery than the coatings produced by prior art methods.

The improved gamma-irradiation induced graft polymerization of NVP, HEMA or mixtures of NVP and HEMA on ocular implant surfaces comprising PMMA to form optimum PVP, P(NVP-HEMA) or PHEMA graft polymer surface modifications thereon comprises carrying out the graft polymerization in an aqueous solution under specific combinations of the following conditions:

(a) monomer concentration in the range of from about 0.5 to about 50%, by weight;

(b) total gamma dose in the range of from about 0.01 to about 0.50 Mrad;

(c) gamma dose rate in the range of from about 10 to about 2,500 rads/minute; and (d) maintaining the molecular weight of the polymer in solution in the range of from about 250,000 to about 5,000,000.

Optimally, the method may also be carried out under one or more of the following conditions:

(e) substantially excluding free oxygen from the aqueous graft polymerization solution;

(f) maintaining the thickness of the PVP or P(NVP-HEMA) surface graft in the range of from about 100 Å to about 150 microns;

(g) including a free radical scavenger in the aqueous graft polymerization solution; and (h) including in the aqueous graft polymerization solution a swelling solvent for PMMA or other polymer substrate surface.

The improved gamma-irradiation induced graft polymerization of NVP, mixtures of NVP and HEMA or HEMA on ocular implant surfaces comprising PP, PVDF, PC or PSi to form optimum PVP or P(NVP-HEMA) surface grafts thereon may also be carried out under specific combinations of the process parameters as indicated above for PMMA but also under conditions which involve excluding free oxygen from the polymerization solution for preferred surface modification of these ocular implant polymer substrates.

The maintenance of the molecular weight of the polymer in solution at certain values, identified in U.S. Pat. No. 4,806,382 as a critical condition of the method, is not actually a "condition" of the method, but rather, as stated in the specification, a result which is dependent on the reaction conditions employed in carrying out the graft polymerization process. It is, therefore, not appropriate to specify the molecular weight of the polymer in solution as a process "condition" since it is rather an outcome of the reaction conditions used in this invention and may be widely varied depending on specific gamma graft monomer-substrate-process conditions. If a certain set of fixed conditions are employed (namely, monomer, monomer concentration, total gamma dose, gamma dose rate and radical polymerization inhibitors), the molecular weight of the polymer formed in solution will be an output of the process which is dependent upon the values of the above-noted monomer, monomer concentration, total gamma dose, gamma dose rate and radical polymerization inhibitor conditions. For example, in the presence of certain ionic monomers, solvents or radical inhibitors, solution polymerization may be significantly inhibited without sacrificing efficient surface graft polymerization and the resulting solution polymer molecular weight may thereby be relatively low (i.e., as low as 5,000–10,000).

Since the application which matured into U.S. Pat. No. 4,806,382 was filed, the inventors of the subject matter defined therein conducted additional research and unexpectedly found that although relatively low doses of 0.01 to 0.20 Mrad are generally preferred for the compositions of this invention, the process could be conducted at a total gamma dose as low as 0.001 Mrad.

The state of the art prior to the application which matured into U.S. Pat. No. 4,806,382 taught the use of relatively high gamma doses, generally greater than 0.5 Mrad, for gamma polymerization grafting and it was, therefore, surprising to find that surface grafting could be achieved at doses as low as 0.01 Mrad. The achievement of effective grafting at doses as low as 0.001 Mrad is, consequently, an even more unexpected result of the process of this invention. Furthermore, although grafting with monomer concentrations as low as 0.5 wt. % was indicated in prior U.S. Pat. No. 4,806,382, further research has revealed that monomer concentrations as low as 0.1 wt. % may be utilized in some embodiments of the graft process of this invention.

The thus improved method and ocular implants are described in U.S. Pat. No. 5,130,160.

In U.S. Pat. No. 5,108,776, it was demonstrated that the methods and ocular implants of the prior art could be further improved by first pre-soaking the ocular implant surface to be surface modified in an aqueous solution of the monomer or the monomer itself in certain cases prior to graft polymerizing the monomer onto the surface from an aqueous monomer solution. More particularly, it was found that pre-soaking the ocular implant material should occur in a solution having a concentration of monomer therein of from about 5 to about 95%, by weight.

In addition, the pre-soaking should be conducted at a temperature in the range of from about 25° to about 90° C. and for from about 0.25 to about 48 hours.

It is an object of the present invention to provide a still further improved ocular implant and method for its manufacture.

SUMMARY OF THE INVENTION

It has been discovered that gamma dose rates much greater than those specified in the above-discussed patents may be employed in carrying out the methods described therein for producing ocular implants.

More particularly, gamma dose rates up to about $10^8$ rads/minute may be employed which enables a significant reduction in the time required to produce the improved ocular implants.

BRIEF DESCRIPTION OF THE DRAWINGS

The drawings.

FIG. 1 depicts a top view of a one-piece intraocular lens,

FIG. 2 depicts a top view of an intraocular lens with fiber haptics which may be made of a different substrate polymer than the optic, and FIG. 3 depicts a top view of a keratoprosthesis.

DETAILED DESCRIPTION OF THE INVENTION

Figure 1:
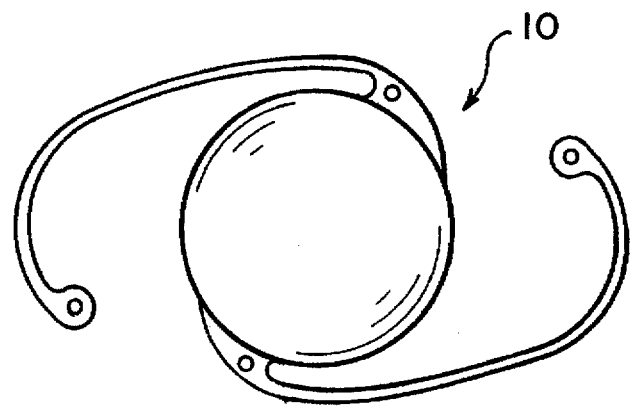
FIGS. 1–3, depict examples of ocular implants according to the present invention.
Figure 2:
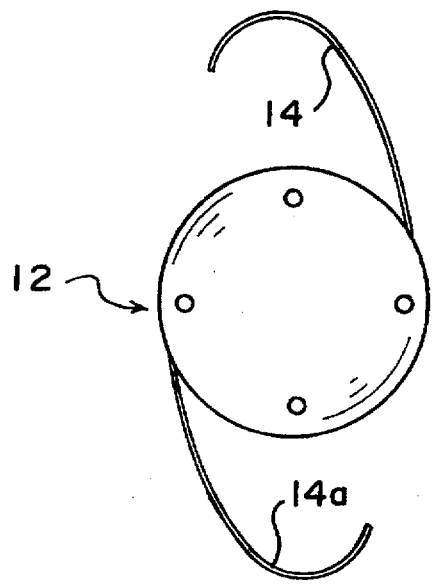
Figure 3:
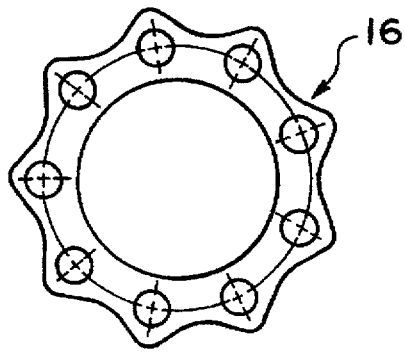

Yalon et al (supra) and Knight et al (supra) disclose gamma-irradiation coatings on PMMA using N-vinylpyrrolidone (NVP) and 2-hydroxyethylmethacrylate (HEMA) and indicate poor dynamic (abrasive) protection of endothelium for these coatings. Dissolvable coatings of polyvinyl-alcohol (PVA) were regarded as optimal for intraocular lenses (IOLs) by Knight et al, supra, and commercial development of a PVA-coated IOL was attempted with unsatisfactory clinical results. The gamma polymerization surface modifications reported were carried out under process conditions of monomer concentration, solvent, dose and dose rate which were not specified and which apparently yielded poor quality, readily abraded coatings. Conditions for producing useful permanent PVP or PHEMA coatings on PMMA IOLs or any other plastic surface are not taught in the prior art. Neither Knight et al, Yalon et al or the literature on gamma-graft polymerization of the past 30 years suggests the process conditions required to achieve the complicated requirements for useful ocular implant coatings. These requirements include:

(a) Thin, permanent, optically clear and uniform graft coatings for the optic. The literature generally discloses conditions which produce distortion and degradation of the substrate due to the use of high gamma-radiation doses (>1 Mrad) and non-aqueous solvent media, and yield thick, cloudy, non-uniform coatings, as well as highly viscous gel-like solutions of the grafting polymer which makes grafted substrate removal and washing very difficult [e.g., Chapiro, Radiation Chemistry of Polymeric Systems, John Wiley and Sons, Inc., New York (1962); Henglein et al, Angew. Chem., Vol. 15, p. 461 (1958) ].

(b) Long-term biocompatibility in the eye (e.g., at least one year satisfactory behavior in rabbit eye implants).

(c) Low contact angle (high wettability) for water or underwater air bubble (less than about 30°).

(d) Less adherent to tissue and to lens epithelial cells from culture (adhesive force to endothelium and number of cells per unit area less than about 50% of that observed for PMMA).

(e) Non-damaging to endothelium (less than ca. 20% damage for in vitro contact tests).

(f) Graft coating may be measurable by ESCA or FTIR spectroscopy or by optical or electron microscopy.

(g) Abrasion resistance by sliding (dynamic) friction testing showing no change in wetting (contact angle) and confirming before and after presence of graft coating.

(h) Rapid hydration—change from dry state to wetted lubricous state on immersion in water (within five minutes).

Yalon et al (supra) disclose an in vitro technique for measuring endothelium damage. Results for PMMA were used to illustrate the method. Although it was noted that PVP coatings reduced cell damage with less damage at higher monomer concentrations, the conditions for the experiment (i.e., irradiation dose, dose rate and the like) were not disclosed, nor were any of the critical process-product relationships indicated.

The improved process conditions and parameters of the invention described in U.S. Pat. No. 4,806,382 which are necessary to produce useful polymers having a surface modified by gamma-irradiation induced graft polymerization therein of PVP, P(NVP-HEMA) or PHEMA include: % monomer, gamma dose, dose rate and oxygen (air) degassing. Other optimal process conditions include catalysts, free radical scavengers, PMMA swelling solvents and temperature. The solution polymer molecular weight and M.W. distribution, the % conversion and residual monomer, the graft polymer thickness and surface properties and the like are process results which can change markedly as the process variables change. For example, the surface modification achieved for PVP on PMMA will be different when using 10% monomer and 0.1 Mrad if prepared at low dose rates since low dose rates (slower polymerization) favor higher molecular weights. Similarly, degassed oxygen-free reaction media result in improved grafts at much lower doses. The presence of free radical scavengers such as copper or iron salts or organic reducing agents (i.e., ascorbic acid) also greatly influences other process parameters, generally reducing solution polymer molecular weight and preventing solution gelation at high monomer concentrations.

Each of the above-described process conditions and parameters of the method of the invention may be varied within the ranges discussed below to produce certain specific combinations which are particularly advantageous for the surface modified ocular article polymers.

(a) Monomer concentration: Increasing monomer concentration increases polymer molecular weight in the graft solution and reduces contact angle (C.A.), i.e., renders the surface more hydrophilic. For example, in the case of forming PVP coatings on PMMA, in the range of from about 3–15% NVP, the PVP viscosity molecular weight ($M_v$) increases from 560,000 to 2,700,000 and the PMMA graft C.A. decreases from 29° to 21° at 0.1 Mrad and 309 rads/minute. However, this effect is sensitive to dose rate and total dose. For example, at 1–10% NVP, but at a lower dose rate of 64 rads/minute, the molecular weight increases from 400,000 to 4,590,000 and the C.A. decreases from 49° to 18°.

In general, monomer concentrations in the range of 0.1–50% are preferred depending on other parameters. Concentrations as low as 0.1–0.5% at low dose rates can yield hydrophilic surface grafts with C.A. below 30–40° under conditions of this invention. At monomer concentrations greater than 20–30%, effective grafting without solution polymer gelation requires low doses and use of free radical scavengers. Monomer concentrations greater than 50% are feasible, but not preferred, since high concentrations of radical scavengers must be used and polymer molecular weights and monomer conversion are lowered significantly by their use. For producing PHEMA coatings, HEMA concentrations of between 0.5% and 10%, by weight, are sufficient.

(b) Dose: In general, increasing total gamma dose increases molecular weight of the polymer and reduces the contact angle. However, an important practical limit exists in that at higher doses, lower dose rates and higher monomer concentrations, reaction media become extremely viscous or form gels which are very difficult to wash and to remove (e.g., about 0.25 Mrad and 10% NVP at 309 rads/minute).

(c) Dose rate: Decreasing gamma radiation dose rate generally increases solution PVP M.W., e.g., from 1,150,000 to 5,090,000 at 10% NVP and 0.1 Mrad as dose rate decreases from 1,235 to 49 rads/minute. The C.A. also goes down at lower dose rates, i.e., from 31° to 15°. As noted above, dose rates of up to $10^8$ rads/minute are practical to considerably shorten the time required to complete the process.

(d) Solution Polymer Molecular Weight: The molecular weight may vary widely depending upon process conditions, weight solution polymer ($M_v$ as low as 5,000–10,000 or less). monomers and radical inhibitors used. Effective grafting with However, solution polymer $M_v$ greater than 5,000, 000 or gels low C.A. may, therefore, be achieved with even low molecular which form during grafting are generally impractical because of washing problems.

(e) Degassing: Removal of oxygen from the graft solutions by vacuum and/or inert gas (e.g., argon purging) has an important effect: lower total doses are required (practical grafting at less than 0.1 Mrad). Oxygen degassing also has a large effect on PVP M.W. and % conversion of monomer. For example, with degassing, good grafting of PVP on polypropylene (PP) is achieved at 0.05 Mrad and 10% NVP (C.A. 15°). Without degassing, little grafting occurs under these conditions. Oxygen degassing is critical to hydrophilic surface modification grafting where the substrate polymer is PP, PVDF or PSi. It has been found that graft polymerization is inefficient when using these materials as substrates in the presence of oxygen. Oxygen degassing is also beneficial for PMMA and PC substrates in that much lower radiation doses (0.01–0.15 Mrad) become effective compared with grafting these polymers in the presence of oxygen.

(f) Graft thickness: Surface grafts less than 100–200 Å, although non-adhesive and hydrophilic, are useful, but may exhibit somewhat less mechanical "softness" or compliant gel-like surfaces than thicker coatings for reduced tissue-contact trauma. Graft coatings greater than ca. 300–500 Å (or 0.03–0.05 microns) up to 50 microns or more are probably more desirable for many applications as long as they are smooth, uniform, optically clear for optic surfaces, and quickly hydrated.

Using no swelling solvents and no prolonged monomer contact with substrates prior to irradiation, surface grafts which exhibit desired implant properties under preferred process conditions have thicknesses of about 0.1 to 5 microns. However, using swelling solvents such as ethyl acetate, polymer grafts on PMMA of 100 microns or more can be prepared. For certain applications, it may be preferred to have thicker "spongy" coatings of 20–100 microns.

(g) Free-Radical Scavengers: Free radical traps, usually reducing agents such as $Cu^+$, $Fe^{+2}$, ascorbic acid and the like, are known to inhibit radical polymerization in solution and thus be effective (especially at high gamma doses, high dose rates and high monomer concentrations) in slowing the onset of solution gelation during grafting. However, under practical grafting conditions, this may result in lower molecular weights, high concentrations of unreacted monomer and broad molecular weight distributions. Use of metal salts may also be objectionable where maximum biocompatibility is critical.

Although most preferred graft conditions avoid the use of radical scavengers, useful conditions for graft coatings of PVP, P(NVP-HEMA) or PHEMA have also been defined using ascorbic acid to limit high viscosity and gelation of the graft polymer solution. These conditions use high monomer concentrations (up to 50%) and thicker grafts are obtained using ethyl acetate as a swelling solvent (0.5–5%).

(h) Swelling solvents: The use of substrate polymer solvents in the aqueous monomer grafting solution facilitates swelling and monomer diffusion into the polymer before and during gamma polymerization. Penetration of monomers into the substrate increases graft coating thickness and enhances bonding to the surface. Solvents such as ethyl acetate have been shown to greatly facilitate this process with some substrates such as PMMA.

Although the above-described method represents a significant improvement over prior art methods, optimum results in each case depend upon the selection of a combination of numerous process parameters and conditions.

The foregoing method is greatly simplified and the surface grafts are significantly enhanced by the method of the present invention according to which the substrate to be surface-modified is pre-soaked in the grafting monomer (or mixture of monomers) or in a first aqueous solution having a concentration of from about 5% to about 95%, by weight, of the grafting monomer (or mixture of monomers) for a period of time and at a temperature sufficient to facilitate diffusion of the monomer(s) into the substrate surface. This pre-soaking step avoids the necessity for utilizing organic swelling solvents. These swelling solvents unduly complicate the final coating procedure since they must be completely washed away and may promote crazing or cracking of the substrate polymers.

The monomer pre-soaking method of the present invention results in a controlled diffusion of monomer into the substrate and may often produce what may be regarded as an interpenetrating subsurface polymer structure for the ultimately formed hydrophilic polymer graft surface modification. The latter is rendered more durable by the thus formed anchoring substructure. This monomer pre-soak improvement is also beneficially conducted with mixed monomers wherein one hydrophilic monomer is used as the pre-soak monomer and a second hydrophilic monomer is used for the subsequent gamma polymerization grafting step. This is particularly advantageous, for example, with polysiloxane surface modification wherein a first monomer pre-soak of a monomer such as diethylaminomethacrylate followed by aqueous NVP present as the medium during gamma irradiation results in a more stable, reproducible, hydrophilic surface for the highly flexible polysiloxane structure.

For PMMA substrates, the pre-soaking is preferably conducted at a temperature of from about 25° to about 80° C. for from about 0.5 to about 24 hours or more (up to about 48 hours) using a first aqueous solution containing from about 5% to about 50%, by weight, of monomer(s) to achieve optimum diffusion thereof into the PMMA substrate.

Where mixtures of NVP and HEMA are employed to form graft copolymerized coatings of P(NVP-HEMA), the mixtures may contain up to about 50% by weight of HEMA, based on the weight of the monomer mixture. However, above 20–30% HEMA, radical scavengers and low monomer concentrations should be used to prevent gelation since HEMA enhances the onset of gelation.

It will be understood by those skilled in the art that the PVP, P(NVP-HEMA) or PHEMA graft coatings of this invention may be modified by copolymerization with various ionic monomers including use of such monomers for the pre-soak step. Mixtures of non-ionic hydrophilic monomers and ionic monomers may also be copolymerized therewith. For example, graft copolymerization incorporating vinylsulfonic acid, styrene sulfonic acid, sulfoethylmethacrylate, sulfopropylmethacrylate or other vinyl sulfonic acids or vinylcarboxylic acids such as acrylic acid, crotonic acid or methacrylic acid can afford surface modifications which are anionic. Similarly, graft copolymerization incorporating basic or aminofunctional monomers, e.g., vinylpyridines, aminostyrenes, aminoacrylates or aminomethacrylates such as dimethylaminomethylmethacrylate or dimethylaminostyrene afford surface modifications which are cationic. It is also useful to use salts of ionic monomers or to convert ionic grafts to the salt form by post-treatment.

Amounts of ionic monomers up to about 50 wt. % of the total monomer weight may be employed, it being understood that the critical process parameters listed above may be maintained.

It will also be understood by those skilled in the art that the ocular implants to be graft coated may also be constructed of materials other than PMMA, PP, PVDF, PC, PSF or PDMSO to facilitate their use. It will be understood by those skilled in the art that such materials may also be at least partially graft polymer surface modified so as to improve their properties as implant materials.

The hydrophilic graft polymer surface modifications of this invention are especially advantageous for intraocular lenses (anterior chamber, posterior chamber and phakic), but are also of great value in affording improved tissue protection and improved biocompatibility for other ocular implants such as corneal inlays, keratoprostheses, epikeratophakia devices, glaucoma drains, retinal staples, scleral buckles and the like.

Based on the foregoing considerations and the many process studies conducted, preferred conditions for various ocular article substrate polymers by way of example are provided below.

In general, choice of the "best" process will depend upon molecular structure of the substrate and grafting polymer, and the coating thickness desired. In general, those conditions which produce extreme solution viscosities and gels or conditions which could produce solvent stress cracking or crazing of the IOL polymers should be avoided. By way of example, the following process conditions are representative of practical conditions for the preparation of improved PVP grafts on various IOL polymer substrates according to this invention.

(a) For PVP grafts on PP, PVDF and PDMSO, or combinations thereof, pre-soak the substrate in NVP monomer at 60° C. for 4 hours followed by graft polymerization in 10% aqueous NVP with about 0.15 Mrad gamma radiation at about 500 rads/minute dose rate, but also as high as $10^8$ rads/minute dose rate.

(b) For PVP grafts on PMMA, PP, PVDF and PDMSO, or combinations thereof, pre-soak the substrate in 40% aqueous NVP monomer at about 60° C. for 4 hours followed by graft polymerization in 10% aqueous NVP with about 0.15 Mrad gamma radiation at about 500 rads/minute dose rate, but also as high as $10^8$ rads/minute dose rate.

(c) For PVP grafts on PMMA, PDMSO and PC, or combinations thereof, pre-soak the substrate in 40% aqueous NVP monomer at about 60° C. for 12 hours followed by graft polymerization in 10% aqueous NVP with about 0.15 Mrad gamma radiation at about 500 rads/minute dose rate, but also as high as $10^8$ rads/minute dose rate.

All percentages expressed in the following non-limiting example are by weight unless otherwise stated.

All contact angles (C.A.) and other surface characteristics for gamma polymerization grafts, unless otherwise indicated, are for samples washed with water or water-alcohol at room temperature or elevated temperatures to remove soluble residual monomer and ungrafted polymer for the improved surface graft processes of this invention. The resulting graft polymers are stable and permanent for long-term ocular implants and are not dissolvable by aqueous media.

It will also be understood by those skilled in the art that the ocular implants to be graft coated may be also constructed of materials other than PMMA, PP, PVDF, PC or PDMSO to facilitate their use. It will be understood by those skilled in the art that such materials may also be at least partially graft polymer surface modified so as to improve their properties as implant materials.

The methods of the invention may be carried out identically to those described in U.S. Pat. Nos. 4,806,382; 4,961,954; 5,108,776; 5,130,160 and 5,290,548 with the exception that dose rates up to $10^8$ rads/minute are employed.

The invention is illustrated by the following non-limiting example.

EXAMPLE

PMMA slab samples were washed twice each by soap solution and distilled water using a sonicator. After complete drying, the samples were put into NVP solutions in glass vials. The samples were then γ-irradiated at various conditions. After γ-irradiation, the surface modified PMMA samples were rinsed several times with H₂O and evaluated.

The polymerized NVP grafting solutions or gels were freeze-dried under a vacuum.

PVP grafted PMMA samples were evaluated by water drop or underwater air bubble contact angle measurements. The bubble technique is regarded as more reliable for very hydrophilic surfaces. For air bubble contact angle, the grafted PMMA was held horizontally in distilled water. An approximately 0.8 µl air bubble was formed and positioned underneath the test surface. Angles on opposite sides of the bubble were measured assuring symmetry. Five measurements were usually made for each sample. The results are set forth in the following table.

TABLE

| | Grafting Solution: 10% NVP | | | |
|---|---|---|---|---|
| Pre-Soak Conditions | Average Dose Rate (rads/min.) | Average Total Dose (Mrad) | Graft Thickness (µm) | Contact Angle (°) |
| None | 16,000 | 0.144 | ≦1 | 24 |
| 20% NVP/60° C./90 min. | 16,000 | 0.144 | 6 | 21 |
| None | 5,129 | 0.135 | ≦1 | 25 |
| 20% NVP/60° C./90 min. | 5,129 | 0.135 | 7 | 22 |

No graft could be visualized by staining on the sample with no pre-soak, which indicates that the penetration depth is one micron or less. However, surface hydrophilicity is achieved as noted by the low contact angle values. This experiment demonstrates the feasibility of using higher dose rates and commercial irradiation facilities for large scale surface modification.

I claim:

1. In a method for modifying the surface of an ocular implant material, said surface consisting essentially of polymethylmethacrylate (PMMA), by the one-step, gamma-irradiation induced polymerized, chemically grafted coating thereon of N-vinylpyrrolidone (NVP), 2-hydroxyethylmethacrylate (HEMA) or a mixture of (NVP) and (HEMA) so as to form a thin, hydrophilic coating of (1) poly-N-vinylpyrrolidone (PVP), (2) poly-2-hydroxyethylmethacrylate (PHEMA) or (3) a copolymer of NVP and HEMA on said surface, the improvement consisting essentially of conducting said one-step, gamma-irradiation induced graft polymerization in a substantially aqueous solution under the following conditions:

(a) monomer concentration in the range of from about 0.1% to about 50%, by weight;

(b) total gamma dose in the range of from about 0.001 to less than about 0.50 Mrad; and (c) gamma dose rate in the range of from above about 2,500 to about $10^8$ rads/minute.

2. The method of claim 1, further including one or more of the following conditions:

(d) substantially excluding free oxygen from said graft polymerization solution;

(e) maintaining the thickness of said polymer coating in the range of from about 100 Å to about 100 microns;

(f) including a free radical scavenger in said aqueous graft polymerization solution; and (g) including in said aqueous graft polymerization solution a swelling solvent for said PMMA surface.

3. In a method modifying the surface of an ocular implant material, said surface consisting essentially of polypropylene (PP), polyvinylidene fluoride (PVDF), a polycarbonate (PC) or a silicone (PSi), by the one-step, gamma-irradiation induced polymerized, chemically grafted coating thereon of N-vinylpyrrolidone (NVP), 2-hydroxyethylmethacrylate (HEMA) or a mixture of (NVP) and (HEMA) so as to form a thin hydrophilic coating of (1) poly-N-vinylpyrrolidone (PVP), (2) poly-2-hydroxyethylmethacrylate (PHEMA) or (3) a copolymer of NVP and HEMA on said surface, the improvement consisting essentially of conducting said one-step, gamma-irradiation induced graft polymerization in a substantially aqueous solution under the following conditions:

(a) monomer concentration in the range of from about 0.1% to about 50% by weight;

(b) total gamma dose in the range of from about 0.001 to less than about 0.50 Mrad;

(c) gamma dose rate in the range of from about 10 to about 2500 rads/minute; and (d) substantially excluding free oxygen from said aqueous graft polymerization solution.

4. The method of claim 3, further including one or more of the following conditions:

(e) maintaining the thickness of said polymer coating in the range of from about 100 Å to about 100 microns;

(f) including a free radical scavenger in said aqueous graft polymerization solution; and (g) including in said aqueous graft polymerization solution a swelling solvent for said surface.

5. The method of claim 1 or 3, wherein said ocular implant material is an intraocular lens.

6. The method of claim 1 or 3, wherein said ocular implant material is a corneal inlay.

7. The method of claim 1 or 3, wherein said ocular implant material is a keratoprosthesis.

8. The method of claim 1 or 3, wherein said ocular implant material is a glaucoma shunt.

9. The method of claim 1 or 3, wherein said ocular implant material is an epikeratophakia device.

10. The method of claim 1 or 3, wherein said ocular implant material is a retinal staple.

11. The method of claim 1 or 3, wherein said ocular implant material is a scleral buckle.

12. The method of claim 1 or 3, wherein said NVP, HEMA or mixture of NVP and HEMA is gamma-irradiation induced copolymerized with an ionic monomer or mixture thereof under said conditions, the total monomer concentration in said solution being in the range of from about 0.1% to about 50%, by weight.

13. The method of claim 12, wherein said ionic monomer is a vinylsulfonic acid or a vinylcarboxylic acid.

14. The method of claim 13, wherein said vinylsulfonic acid is sulfoethylmethacrylate, sulfopropylmethacrylate, styrene sulfonic acid or vinyl sulfonic acid.

15. The method of claim 13, wherein said vinylcarboxylic acid is acrylic, methacrylic or crotonic acid.

16. The method of claim 12, wherein said ionic monomer is an amino-functional monomer.

17. The method of claim 16, wherein said amino-functional monomer is a vinylpyridine, an aminostyrene, an aminoacrylate or an aminomethacrylate.

18. The method of claim 1 or 3, including the step of pre-soaking said ocular implant material in at least one of said monomers or in a first aqueous solution of at least one of said monomers, having a concentration of monomer therein of from about 5% to about 95%, by weight, prior to conducting said gamma-irradiation induced graft polymerization, said pre-soaking being conducted for a period of time and at a temperature sufficient to facilitate diffusion of said monomer or monomers into said ocular implant material.

19. The method of claim 18, wherein said pre-soaking step is conducted at a temperature in the range of from about 25° to about 90° C.

20. The method of claim 18, wherein said pre-soaking is conducted for a period of time from about 0.25 to about 48 hours.

21. An ocular implant prepared according to the method of claim 1.

22. An ocular implant according to claim 21, wherein said ocular implant is an intraocular lens, a corneal inlay, a keratoprosthesis, an epikeratophakia device, a glaucoma shunt, a retinal staple or a scleral buckle.

* * * * *